US008557933B2

(12) United States Patent
Hagadorn et al.

(10) Patent No.: US 8,557,933 B2
(45) Date of Patent: Oct. 15, 2013

(54) METHODS FOR PREPARATION OF PYRIDYLAMINES AND THEIR USE IN OLIGOMERIZATION REACTIONS

(75) Inventors: John Robert Hagadorn, Houston, TX (US); Timothy Marlow Boller, Houston, TX (US); Steven Douglas Brown, Houston, TX (US); Gary Michael Diamond, Menlo Park, CA (US); Keith Anthony Hall, San Jose, CA (US); James Martin Longmire, San Jose, CA (US); Lily Joy Ackerman, San Francisco, CA (US); Susan Jessica Schofer, San Francisco, CA (US); Eric Lee Kuiokalani Dias, Belmont, CA (US); Andrew Cottone, III, Middletown, DE (US); Carl Edgar Whittle, Chadds Ford, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/486,483

(22) Filed: Jun. 1, 2012

(65) Prior Publication Data

US 2012/0238713 A1 Sep. 20, 2012

Related U.S. Application Data

(62) Division of application No. 12/192,843, filed on Aug. 15, 2008, now Pat. No. 8,212,047.

(60) Provisional application No. 60/973,965, filed on Sep. 20, 2007.

(51) Int. Cl.
*C08F 10/14* (2006.01)
*C07D 213/38* (2006.01)

(52) U.S. Cl.
USPC .............. 526/75; 546/329; 546/345; 585/510

(58) Field of Classification Search
None
See application file for complete search history.

(56) References Cited

U.S. PATENT DOCUMENTS

| 6,713,577 | B2 | 3/2004 | Boussie et al. | |
|---|---|---|---|---|
| 6,750,345 | B2 | 6/2004 | Boussie et al. | |
| 7,045,583 | B2 | 5/2006 | Kuchta et al. | |
| 7,638,671 | B2 * | 12/2009 | McConville et al. | 585/513 |
| 2007/0185358 | A1 | 8/2007 | Buchanan et al. | |
| 2007/0185360 | A1 | 8/2007 | Buchanan et al. | |
| 2007/0185361 | A1 | 8/2007 | Buchanan et al. | |
| 2007/0185362 | A1 | 8/2007 | Lattner et al. | |
| 2007/0185364 | A1 | 8/2007 | Buchanan et al. | |

FOREIGN PATENT DOCUMENTS

| WO | 2006062972 | 6/2006 |
|---|---|---|
| WO | WO 2006096881 A1 * | 9/2006 |

OTHER PUBLICATIONS

Jahn, U.; Andersch, J.; Schroth, W. "3,3-Dichloroprop-2-ene Iminium Salts (Vinylogous Viehe Salts): A Study of Their Reactivity Towards Nucleophiles" *Synthesis* 1997, 5, 573-588.
Yamauchi, T.; Sazanami, H.; Sasaki, Y.; Higashiyama, K. "Diastereoselective addition of organolithiums to 1,3-oxazolidines complexed with aluminum tris (2,6-diphenylphenoxide) (ATPH)" *Tetrahedron* 2005, 61, 1731-1736.
Hasegawa, M.; Taniyama, D.; Tomioka, K. "Facile Asymmetric Synthesis of α-amino Acids Employing Chiral Ligand-Medicated Asymmetric Addition Reachtion of Phenyllithium with Imines" *Tetrahedron* 2000, 56, 10153-10158.
Taniyama, D.; Hasegawa, M.; Tomioka, K. "A facile asymmetric synthesis of 1-substituted tetrahydroisoquinoline based on a chiral ligand-mediated addition of organolithium to imine" *Tetrahedron Asymmetry* 1999, 10, 221-223.
Gibson, V.C., Spitzmesser, S.K. "Advances in non-metallocene olefin polymerization catalysis"; *Chem Rev.* 2003, 103, 283-315.
Gros, P.; Fort, Y. "Amitioalkoxide-mediated formation and stabilization of phenylpyridyllithium; straightforward access to phenylpridine derivatives" *J. Org. Chem* 2003, 68, 2028-2029.
Boehme, H.; Graetzel vol Graetz, J "Darstellung, Eigenschaften Und Umsetzungen Von (B-Alkoxycarbonyl-Alkyliden) Ammoniumsalzen" *Tetrahedron* 1977, 33, 841-845.
Saito, S.; Hatanaka, K.; Yamamoto, H. "Nucleophilic Addition of Organomagnesiums to Aldimines: Scandium Triflate (Sc(OTf)3) as an Effective Catalyst" *Synlett* 2001, 12, 1859-1861.
Domski, G.J.; Lobkovsky, E.B.; Coates, G.W. "Polymerization of α-olefins with pyridylamidohafnium catalysts: living behavior and unexpected isoselectivity from a $C_s$-symmetric catalyst precursor" *Macromolecules* 2007, 40, 3510-3513.
Gilman, H.; Kirby, R. H. "The Relative Reactivities of Organolithium and Organomagnesuim Compounds" *J. Am. Chem. Soc.* 1933, 55, 1265-1270.

* cited by examiner

*Primary Examiner* — Zinna Northington Davis
(74) *Attorney, Agent, or Firm* — Kristina M. Leavitt; Samuel E. Shehadeh; Leandro Arechederra, III

(57) ABSTRACT

Alternate methods for preparing functionalized pyridylamine products from pyridinyl starting materials are provided herein. These alternately-prepared functionalized pyridylamines can be used as ligands or ligand precursors in catalytic compositions, e.g., in oligomerization reactions. Methods for such reactions are also provided herein.

14 Claims, No Drawings

METHODS FOR PREPARATION OF PYRIDYLAMINES AND THEIR USE IN OLIGOMERIZATION REACTIONS

CROSS REFERENCE TO RELATED APPLICATIONS

This application is a divisional of U.S. Ser. No. 12/192,843 filed on Aug. 15 2008, now U.S. Pat. No. 8,212,047,which claims the benefit of and priority from U.S. Ser. No. 60/973, 965, filed on Sep. 20, 2007, the disclosure of which is hereby incorporated herein in its entirety.

FIELD OF THE INVENTION

This invention relates generally to alternate methods for preparing functionalized pyridyl-amine products from pyridinyl starting materials. In addition, this invention further relates to the use of these functionalized pyridyl-amines as ligands or precursors in alkene oligomerization reactions.

BACKGROUND OF THE INVENTION

Pyridylamine compounds are known in the prior art. Indeed, their synthesis schemes can often depend on the nature of the substitutions on various portions of the pyridylamine molecule. Whatever the synthesis route, pyridylamines have been used in a variety of applications. Some examples of their use in catalytic compositions, and methods of forming such catalytic compositions, can be found, e.g., in U.S. Pat. Nos. 6,750,345 and 6,713,577. These patents disclose ligands, complexes, compositions and/or catalysts that provide enhanced olefin polymerization capabilities based on a substituted pyridyl amine structure and hafnium. Other examples of methods of using pyridylamine-containing catalytic compositions for oligomerization reactions can be found, e.g., in U.S. Patent Application Publication Nos. 2007/0185358, 2007/0185360, 2007/0185361, 2007/0185362, and 2007/0185364.

Though some pyridylamines can be manufactured by synthesis routes that are acceptable for bench-scale syntheses, there is a need for alternate synthesis routes that have economic and scale-up advantages for more commercial-scale efforts. The alternate synthesis routes described herein tend to focus on three aspects of improvement: reaction chemistry (e.g., nature of reactants and catalytic/facilitating compounds), temperature control, and number/yield of synthesis steps.

SUMMARY OF THE INVENTION

In one aspect of the present invention, a method is provided for synthesizing a functionalized pyridyl-amine product comprising the following steps:
(a) providing a di-substituted pyridine reactant having the following formula:

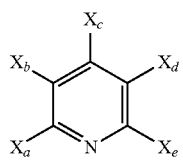

where $X_b$, $X_c$, and $X_d$ are each independently selected from hydrogen and optionally substituted linear, branched, cyclic, heterocyclic, and/or aromatic hydrocarbyl, where at least one of $X_a$ and $X_e$ is a halide, where $X_a$ and $X_e$ can be the same or different, and where, when one of $X_a$ and $X_e$ is not a halide, the one of $X_a$ and $X_e$ that is not a halide is an optionally substituted aryl moiety, preferably provided that the optional substitution(s) on the aryl moeity and on the hydrocarbyl moiety(ies) are not polar substitutions.
(b) selectively activating one of the $X_a$ and $X_e$ halide moieties on the di-substituted pyridine under conditions sufficient to form an activated and substituted pyridine intermediate; and
(c) reacting the activated and substituted pyridine intermediate with one or more other reactants under conditions sufficient to form the functionalized pyridyl-amine product.

In another aspect of the present invention, a method is provided for synthesizing a functionalized pyridyl-amine product comprising the following steps:
(a) providing a di-substituted pyridine reactant having the following formula:

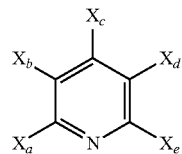

where $X_b$, $X_c$, and $X_d$ are each independently selected from hydrogen and optionally substituted linear, branched, cyclic, heterocyclic, and/or aromatic hydrocarbyl, preferably provided that any of the optional substitutions on the hydrocarbyl moiety(ies) are not polar substitutions, and where both of $X_a$ and $X_e$ are halides (e.g., independently selected from bromine and iodine).
(b) selectively activating one of the $X_a$ and $X_e$ halide moieties on the di-substituted pyridine under conditions sufficient to form a mono-metallated, halo-substituted pyridine intermediate;
(c) reacting the mono-metallated, halo-substituted pyridine intermediate with one or more other reactants under conditions sufficient to form a halo-substituted pyridinyl aldehyde intermediate;
(d) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate; and
(e) aminating the (optionally substituted aryl)-substituted pyridinyl aldehyde intermediate by contacting it with one or more other reactants under conditions sufficient to form the functionalized pyridyl-amine product.

In still another aspect of the present invention, a method is provided for synthesizing a purified functionalized pyridyl-amine product comprising the following steps:
(a) providing a di-substituted pyridine reactant having the following formula:

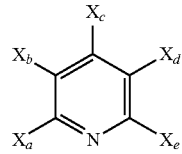

where $X_b$, $X_c$, and $X_d$ are each independently selected from hydrogen and optionally substituted linear, branched, cyclic, heterocyclic, and/or aromatic hydrocarbyl, preferably provided that any of the optional substitutions on the hydrocarbyl moiety(ies) are not polar substitutions, and where both of $X_a$ and $X_e$ are halides.

(b) selectively activating one of the $X_a$ and $X_e$ halide moieties on the di-substituted pyridine under conditions sufficient to form a mono-metallated, halo-substituted pyridine intermediate;

(c) reacting the mono-metallated, halo-substituted pyridine intermediate with one or more other reactants under conditions sufficient to form a halo-substituted pyridinyl aldehyde intermediate;

(d) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate;

(e) aminating the (optionally substituted aryl)-substituted pyridinyl aldehyde intermediate by contacting it with one or more other reactants under conditions sufficient to form the crude functionalized pyridyl-amine product;

(f) treating the crude functionalized pyridyl-amine product with an acid to form a functionalized pyridyl-ammonium product salt;

(g) triturating the functionalized pyridyl-ammonium product salt to remove impurities; and (h) treating the isolated, functionalized pyridyl-ammonium product salt with a base to form a purified functionalized pyridyl-amine product.

These aspects of the invention, as described further herein, can empower more highly economical and/or more easily scaled up syntheses of functionalized pyridyl-amines, which can then be used as ligands in catalytic compositions for oligomerizing $C_2$ to $C_{12}$ alkenes (e.g., olefins such as ethylene).

DETAILED DESCRIPTION OF THE PREFERRED EMBODIMENTS

As used herein, the new numbering scheme for the Periodic Table Groups is used as set out in CHEMICAL AND ENGINEERING NEWS, 63 (5), 27 (1985).

As used herein, the term "about," whether in reference to a single value or a range of values, is defined according to the scope of the value(s) given the significant figures expressed. For instance, "about 99%" means from 98.50% to 99.49%; "about 99.0%" means from 98.950% to 99.049%; and "about 99.00%" means from 98.9950% to 99.0049%.

As used herein, the phrase "characterized by the formula" is not intended to be limiting and is used in the same way that "comprising" is commonly used. The term "independently selected" is used herein to indicate that the groups in question—e.g., $R_1$, $R_2$, $R_3$, $R_4$, and $R_5$—can be identical or different (e.g., $R_1$, $R_2$, $R_3$, $R_4$, and $R_5$ may all be substituted alkyls, or $R_1$ and $R_2$ may be a substituted alkyl and $R_3$ may be an aryl, etc.). Use of the singular includes use of the plural and vice versa (e.g., a hexane solvent, includes hexanes). A named R group will generally have the structure that is recognized in the art as corresponding to R groups having that name. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When an adjectival term, such as "substituted," introduces a list of possible substituted groups, it is intended that the term apply to every member of that group. For example, the phrase "substituted alkyl, alkenyl, and alkynyl" is to be interpreted as "substituted alkyl, substituted alkenyl and substituted alkynyl." Similarly, "optionally substituted alkyl, alkenyl, and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" as used herein refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can include 1-naphthyl or 2-naphthyl; "anthracenyl" can include 1-anthracenyl, 2-anthracenyl or 9-anthracenyl; and "phenanthrenyl" can include 1-phenanthrenyl, 2-phenanthrenyl, 3-phenanthrenyl, 4-phenanthrenyl, or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyridine, pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds., Elsevier, 2d. ed., 1996.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene, and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. The term "heteroatom-containing" is considered an adjectival term herein and is thus treated similarly to the term "substituted."

Throughout the instant specification, several abbreviations may be used to refer to specific compounds or elements. Abbreviations for atoms are as given in the periodic table (Li=lithium, for example). Other abbreviations that may be used are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TsOH" to refer to para-toluenesulfonic acid; "cat." to refer to catalytic amount of; "LDA" to refer to lithium diisopropylamide; "DMF" to refer to dimethylformamide; "eq." to refer to molar equivalents; "TMA" to refer to AlMe$_3$; "TIBA" to refer to Al i-(Bu)$_3$; and the like.

In one aspect of the present invention, a method is provided for synthesizing a functionalized pyridyl-amine product comprising the following steps:

(a) providing a di-substituted pyridine reactant having the following formula:

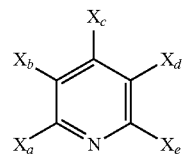

where $X_b$, $X_c$, and $X_d$ are each independently selected from hydrogen and optionally substituted linear, branched, cyclic, heterocyclic, and/or aromatic hydrocarbyl, where at least one of $X_a$ and $X_e$ is a halide, where $X_a$ and $X_e$ can be the same or different, and where, when one of $X_a$ and $X_e$ is not a halide, the one of $X_a$ and $X_e$ that is not a halide is an optionally substituted aryl moiety, preferably provided that the optional substitution(s) on the aryl moeity and on the hydrocarbyl moiety(ies) are not polar substitutions.

(b) selectively activating one of the $X_a$ and $X_e$ halide moieties on the di-substituted pyridine under conditions sufficient to form an activated and substituted pyridine intermediate; and (c) reacting the activated and substituted pyridine intermediate with one or more other reactants under conditions sufficient to form the functionalized pyridyl-amine product.

In one preferred embodiment of this aspect of the invention, the reacting in step (c) occurs in a single reaction step, e.g., with the intermediate being contacted with an imine and/or an iminium compound having the following formulas:

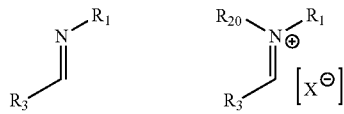

under conditions sufficient to form the pyridyl-amine compound in a single reaction step.

Additionally or alternately, the activated and substituted pyridine intermediate formed in step (b) can be substituted at one of the $X_a$ and $X_e$ positions with an alkali metal such as lithium and at the other of the $X_a$ and $X_e$ positions with either a halide or an optionally substituted aryl moiety. As such, in this embodiment, the di-substituted pyridine is reacted in step (b) with an alkyl-alkali metal organometallic compound, such as n-butyllithium or sec-butyllithium.

Further, additionally or alternately, one of $X_a$ and $X_e$ in step (a) is an optionally substituted aryl moiety, such as a phenyl moiety, and the other of $X_a$ and $X_e$ is a halide, preferably selected from bromine and iodine. In this case, the di-substituted pyridine would comprise an optionally-substituted-aryl-halo-pyridine compound.

As a result, in the preferred embodiment of this aspect of the invention, and particularly when an imine/iminium compound is used in step (c) and when one of $X_a$ and $X_e$ is an optionally substituted aryl moiety and the other of $X_a$ and $X_e$ is a halide in step (a), the method can preferably consist essentially of two reaction steps, i.e., steps (b) and (c). To clarify, in this embodiment, although there may be essentially only two reaction steps, other non-reaction steps, e.g., providing reactants and isolating/purifying products and intermediates, are expressly included in this embodiment of method.

In another aspect of the present invention, a method is provided for synthesizing a functionalized pyridyl-amine product comprising the following steps:
(a) providing a di-substituted pyridine reactant having the following formula:

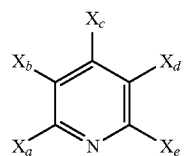

where $X_b$, $X_c$, and $X_d$ are each independently selected from hydrogen and optionally substituted linear, branched, cyclic, heterocyclic, and/or aromatic hydrocarbyl, preferably provided that any of the optional substitutions on the hydrocarbyl moiety(ies) are not polar substitutions, and where both of $X_a$ and $X_e$ are halides (e.g., independently selected from bromine and iodine).
(b) selectively activating one of the $X_a$ and $X_e$ halide moieties on the di-substituted pyridine under conditions sufficient to form a mono-metallated, halo-substituted pyridine intermediate;
(c) reacting the mono-metallated, halo-substituted pyridine intermediate with one or more other reactants under conditions sufficient to form a halo-substituted pyridinyl aldehyde intermediate;
(d) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate; and
(e) aminating the (optionally substituted aryl)-substituted pyridinyl aldehyde intermediate by contacting it with one or more other reactants under conditions sufficient to form the functionalized pyridyl-amine product.

In a particularly preferred embodiment of this aspect of the invention, the di-substituted pyridine can be selectively activated by contacting it in step (b) with a hydrocarbyl-mixed metal organometallic compound. In this particularly preferred embodiment, the mixed metal portion of the organometallic compound comprises, or consists essentially of, at least one alkali metal, such as lithium, and at least one divalent or trivalent metal, such as selected from groups 2 and 13 of the Periodic Table of Elements (e.g., beryllium, magnesium, calcium, boron, aluminum, or the like). Additionally or alternately, in this particularly preferred embodiment, the number of hydrocarbyl moieties in the organometallic compound should correspond to, and typically equals, the sum of the valences of the metals in the mixed metal portion of the organometallic compound, unless one or more of the hydrocarbyl moieties are joined together to form a heterocycle with one or more of the metals in the mixed metal portion of the organometallic compound. In this particularly preferred embodiment, the hydrocarbyl-mixed metal organometallic compound can be used to selectively convert one of the $X_a$ and $X_e$ halide moieties to a metal-containing moiety. If the metal-containing moiety comprises the alkali metal, which is monovalent, then the metal-containing moiety should consist solely of the alkali metal. However, if the metal-containing moiety comprises the divalent/trivalent metal, then the metal-containing moiety can be a monovalent version of the divalent/trivalent metal, which should typically be attached to one or more hydrocarbyl groups to satisfy the remaining valence, but which may additionally or alternately be attached to another one or more other di-substituted pyridine molecules, thereby activating them as well.

In the aforementioned particularly preferred embodiment of this aspect of the invention, or alternatively in another particularly preferred embodiment of this aspect of the invention, the selective activation in step (b) of one of the halide moieties in the di-substituted pyridine can be accomplished through contact with one or more reagents at a temperature above −78° C., preferably above −40° C., more preferably above −25° C., for example between −25° C. and 10° C. or between −20° C. and 0° C. It is believed that, through enabling reaction temperature in step (b) to be above −78° C., a synthesis method can be attained that is more economical and/or that can scale up (i.e., producing functionalized pyridyl-amine product on a scale larger than bench scale) more easily.

Additionally or alternately, in this aspect of the invention, the aminating step (e) can be accomplished in two distinct reaction steps, as follows:
(e1) reacting the (optionally substituted aryl)-substituted pyridinyl aldehyde intermediate with a substituted amine having the formula $(R_1)(R_{20})NH$ under conditions sufficient to form a pyridyl-amine/pyridyl-iminium intermediate;
(e2) reacting the pyridyl-amine/pyridyl-iminium intermediate with a metal hydrocarbyl compound under conditions sufficient to form the functionalized pyridyl-amine product.

The purification of crude pyridyl-amine products prepared using the methods described herein (and elsewhere) may be accomplished by column chromatography using adsorbents, e.g., silica gel, basic alumina, or the like. Alternatively, the crude pyridyl-amine products may be triturated to form a purified pyridyl-amine product. The term "trituration" is used herein to describe general processes that result in purification of a substance by the extraction or washing away of impurities. This generally requires that the product to be purified exists in a different phase (e.g., solid phase versus liquid phase, or aqueous phase versus organic phase) than the wash. In a first alternate embodiment, the trituration can include merely solidifying the crude pyridyl-amine product from solution. In a second alternate embodiment, the crude pyridyl-amine products can be purified by a process including acid treatment of the crude pyridyl-amine product to form a product salt, isolation of the product salt via a non-chromatographic method, and basic treatment of the isolated product salt to form a purified pyridyl-amine product. In this second alternate embodiment, the alternative process can begin with the protonation of the pyridyl-amine with an acid (e.g., an organic acid, such as maleic acid, citric acid, or the like; an inorganic acid such as hydrochloric acid or the like; or a combination thereof), to form a salt of the pyridyl-amine, which can be referred to as a pyridyl-ammonium salt. In this second alternate embodiment, the pyridyl ammonium salt produced may then be triturated, or isolated as a solid, optionally but preferably washed, and, if necessary, (re)crystallized to form a purified pyridyl ammonium salt. Further, in this second alternate embodiment, this purified pyridyl ammonium salt may then be reacted with a basic reagent, e.g., a hydroxide salt such as sodium hydroxide, to form the purified pyridyl-amine (and a byproduct salt that should be easily separated therefrom). In either of these alternate embodiments, therefore, the purified pyridyl-amine product may be obtained without the use of column chromatography. Example 2, for instance, exemplifies the second alternate purification method.

In either or both of the aforementioned aspects of the invention, the functionalized pyridyl-amine products can be further used, whether as synthesized or in purified form, as ligands and/or ligand precursors in catalytic compositions for oligomerizing $C_2$ to $C_{12}$ alkenes (e.g., olefins such as ethylene). Some examples of such catalytic compositions, and methods of forming such catalytic compositions, can be found, e.g., in U.S. Patent Application Publication No. 2006/0247403, which is incorporated herein by reference in its entirety. Other examples of methods of using such catalytic compositions in oligomerizing $C_2$ to $C_{12}$ alkenes can be found, e.g., in U.S. Patent Application Publication Nos. 2007/0185358, 2007/0185360, 2007/0185361, 2007/0185362, and 2007/0185364, as well as in U.S. Application Ser. No. 60/873,221, the disclosures of each of which are hereby incorporated herein.

A method for forming an olefin oligomer using a pyridylamine-containing catalytic composition can include, but is not limited to: (a) synthesizing, and optionally purifying, a functionalized pyridyl-amine product by a method according to one of the aforementioned aspects of the invention; (b) forming a metal-ligand precursor by contacting the pyridylamine product with a metal precursor compound, e.g., wherein the metal comprises one or more elements from Groups 4-10 of the Periodic Table of Elements (preferably from Groups 4, 6, and 8-10, more preferably comprising chromium, hafnium, titanium, and/or zirconium; particularly preferably comprising, or consisting essentially of, chromium), and optionally also with an activator; (c) contacting an olefin feed with said metal-ligand precursor under reaction conditions sufficient to produce an effluent comprising a trimerized and/or tetramerized olefin product; and (d) optionally isolating and/or purifying the trimerized and/or tetramerized olefin product.

Specifically, this invention relates to the trimerizing and/or tetramerizing of ethylene to form 1-hexene and/or 1-octene using the ligands and/or ligand precursors described herein. Preferred ligands for use in the trimerizing and/or tetramerizing of ethylene can include, but are not limited to, pyridylamine ligands such as those shown in FIGS. 6-12 of U.S. Patent Application Publication No. 2007/0185362 (labeled as A1-A75), especially ligands A4, A5, A23, A28, A29, A30, and A38 therein.

Once the desired ligand is formed, it can be combined with a Cr atom, ion, compound, or other Cr precursor compound, and, in some embodiments, the present invention encompasses compositions that include any of the above-mentioned ligands, in combination with an appropriate Cr precursor and an optional activator.

Particularly useful Cr metal precursor compounds are represented by the formula $Cr(L)_n$, where L is an organic group, an inorganic group, or an anionic atom, and where n is an integer of 1 to 6, and, when n is not less than 2, each L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups can be joined into a ring structure. One or more of the ligands L may be ionically bonded to Cr and, for example, L may be a non-coordinated, loosely-coordinated, or weakly-coordinated anion (e.g., L may be selected from the group consisting of those anions described below in the conjunction with the activators). See Marks et al., *Chem. Rev.* 100, pp 1391-1434 (2000) for a detailed discussion of these weak interactions. The chromium precursors may be monomeric, dimeric, or higher orders thereof.

In a preferred embodiment, each L is independently a hydrocarbyl, halide, alkoxy, carboxylate, diaonate, amino, ether, or amine. In an alternate embodiment, each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$—O—$NMe_2$, trifluoroacetate, $CH(SiMe_3)_2$, p-tolyl, diisopropylamide, picolinate, or $NO_3$, where Et is ethyl and Me is methyl.

Specific examples of suitable chromium precursors include, but are not limited to, $(THF)_3CrMeCl_2$, $(Mes)_3Cr(THF)$, $[\{TFA\}_2Cr(OEt_2)]_2$, $(THF)_3CrPh_3$, $CrCl_3(THF)_3$, $CrCl_4(NH_3)_2$, $Cr(NMe_3)_2Cl_3$, $CrCl_3$, $Cr(acac)_3$, $Cr(2\text{-ethyl-hexanoate})_3$, $Cr(neopentyl)_4$, $Cr(CH_2\text{—}C_6H_4\text{-o-}NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3[CrPh_6][Li(THF)]_3$, $[CrPh_6][Li(n\text{-}Bu_2O)]_3$, $[Cr(C_4H_8)_3][Li(THF)]_3$, and other well known chromium compounds commonly used as precursors in the formation of Cr complexes and catalysts.

Preferred metal precursors used herein can be selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, and mixtures thereof.

The ligand may be mixed with a metal precursor compound prior to, or simultaneously with, allowing the mixture to be contacted with the reactants (e.g., monomers). The ligand to metal precursor compound ratio can be in the range of about 0.01:1 to about 100:1, more specifically in the range of about 0.1:1 to about 10:1.

In some embodiments, the ligand may be mixed with a suitable metal precursor prior to, or simultaneous with, allowing the mixture to be contacted to the reactants. When the ligand is mixed with the metal precursor, a metal-ligand complex can be formed. In connection with the metal-ligand complex and depending on the ligand(s) chosen, the metal-ligand complex may take the form of dimers, trimers, or higher orders thereof, or there may be two or more metal atoms that are bridged by one or more ligands. Furthermore, two or more ligands may coordinate with a single metal atom. The exact nature of the metal-ligand complex(es) formed can depend on the chemistry of the ligand and on the method of combining the metal precursor and ligand, such that a distribution of metal-ligand complexes may form, with the number of ligands bound to the metal being greater than, equal to, or less than the number of equivalents of ligands added relative to an equivalent of metal precursor.

In one embodiment, metal ligand complexes (such as the Cr-ligand complex described above) can advantageously coordinate such that the metal (e.g., Cr) is associated with (e.g., covalently and/or datively bonded to) the pyridyl nitrogen atom, the amine nitrogen atom, one or more atoms of the optionally substituted aryl group attached to the pyridine, or any combination thereof.

The ligand-metal-precursor combinations and the metal ligand complexes, described above, are optionally activated in various ways to yield compositions active for selective oligomerization (preferably ethylene oligomerization). For the purposes of this patent specification and appended claims, the terms "cocatalyst" and "activator" are used herein interchangeably and are defined to be any compound which can activate any one of the ligands-metal-precursor-combinations and the metal ligand complexes described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide, or amide. Mixtures of different alumoxanes and modified alumoxanes may also be used. For further descriptions on production and use of alumoxanes, see U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, and 5,329,032; see also European Publication Nos. EP 0 561 476 A1, EP 0 279 586 B1, EP 0 516 476 A1, and EP 0 594 218 A1; see also International Publication No. WO 94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio can be from 1000:1 to 100:1.

It may be preferable to use a visually clear methylalumoxane. A cloudy or gelled alumoxane can be filtered to produce a clear solution, or clear alumoxane can be decanted from the cloudy solution. Another particularly useful alumoxane is a modified methyl alumoxane (MMAO) cocatalyst type 3A (commercially available from Akzo Chemicals, Inc., under the trade name Modified Methylalumoxane type 3A, and disclosed in U.S. Pat. No. 5,041,584).

Aluminum alkyl or organoaluminum compounds which may be utilized as activators (or scavengers) include, but are not limited to, trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide, and the like.

Other ionizing activators, group 13 reagents, divalent metal reagents, and alkali metal reagents can be used, additionally or in lieu of alumoxane activators. Examples of such activators, as well as information about their practical use in oligomerization systems, can be found, e.g., in U.S. Patent Application Publication No. 2007/0185362.

An advantageous method for preparing alpha olefin comonomers from an olefin such as ethylene can comprise the following steps: providing one or more comonomer synthesis reactors configured in series, and one or more downstream gas/liquid phase separators configured in series; feeding olefin (e.g., ethylene) and a catalyst in a solvent and/or diluent to the one or more comonomer synthesis reactors; reacting in the one or more comonomer synthesis reactors the ethylene and the catalyst in said solvent and/or diluent under reaction conditions sufficient to produce an effluent stream comprising one or more desired comonomers; passing the effluent stream to the one or more downstream gas/liquid phase separators to form a gas stream comprising the unreacted olefin (e.g., ethylene), and a liquid stream comprising the comonomer(s); optionally recycling to the one or more comonomer synthesis reactors the unreacted olefin (e.g., ethylene) and optionally a portion of the liquid stream; storing at least a portion of the liquid stream for subsequent processing of the comonomer(s); and purifying at least a portion of said liquid stream by removing at least one of solid polymer, catalyst, catalyst activator(s), catalytic decomposition products, and undesirable olefins therefrom, wherein the comonomer(s) is(are) selected from the group consisting of 1-butene, 1-hexene, 1-octene, 1-decene, and mixtures thereof, and is(are) similar in composition to the solvent and/or diluent.

Another advantageous method for preparing alpha olefin comonomers from an olefin such as ethylene can comprise the following steps: providing one or more comonomer synthesis reactors configured in series, one or more downstream gas/liquid phase separators configured in series, and one or more distillation columns configured in series; feeding olefin (e.g., ethylene) and a catalyst in a solvent and/or diluent to the one or more comonomer synthesis reactors; reacting in the one or more comonomer synthesis reactors the olefin (e.g., ethylene) and the catalyst in the solvent and/or diluent under reaction conditions sufficient to produce an effluent stream comprising one or more desired comonomers; passing the effluent stream to the one or more downstream gas/liquid phase separators to form a gas stream comprising the unreacted olefin (e.g., ethylene), and a liquid stream comprising the comonomer(s); purifying at least a portion of the liquid stream by removing at least one of solid polymer, catalyst, catalyst activator(s), catalytic decomposition products, and undesirable olefins therefrom; passing at least a portion of the liquid stream to the one or more distillation columns to separate the comonomer product; optionally recycling to the one or more comonomer synthesis reactors the unreacted olefin (e.g., ethylene) and optionally the catalyst and the solvent and/or diluent; and storing the comonomer product for subsequent processing, wherein the comonomer(s) is(are) selected from the group consisting of 1-butene, 1-hexene, 1-octene, 1-decene, and mixtures thereof.

Yet another advantageous method for preparing alpha olefin comonomers from an olefin such as ethylene, which comprises the following steps: providing a combination comonomer synthesis reactor and gas/liquid phase separator into a single vessel; feeding olefin (e.g., ethylene) and a catalyst in a solvent and/or diluent to the combination comonomer synthesis reactor and gas/liquid phase separator; reacting in the combination comonomer synthesis reactor and gas/liquid phase separator the olefin (e.g., ethylene) and the catalyst in the solvent and/or diluent under reaction conditions sufficient to produce an effluent stream comprising a gas stream comprising unreacted olefin (e.g., ethylene) and a liquid stream comprising one or more desired comonomers; optionally recycling to the combination comonomer synthesis reactor and gas/liquid phase separator the gas stream and optionally at least a portion of the liquid stream; purifying at least a portion of said liquid stream by removing at least one of solid polymer, catalyst, catalyst activator(s), catalytic decomposition products, and undesirable olefins therefrom; and storing at least a portion of the liquid stream for subsequent processing of the comonomer(s), wherein the comonomer(s) is(are) selected from the group consisting of 1-butene, 1-hexene, 1-octene, 1-decene, and mixtures thereof.

Still another method for generating 1-hexene and other desired comonomers immediately before a polyethylene polymerization reactor can include the steps of: providing an in-line comonomer synthesis reactor and a downstream gas/liquid phase separator prior to a polyethylene polymerization reactor; feeding ethylene monomer and a catalyst in a solvent and/or diluent to said comonomer synthesis reactor; reacting said ethylene and said catalyst in solvent and/or diluent under reaction conditions sufficient to produce an effluent stream comprising one or more desired comonomer(s), e.g., selected from the group consisting of 1-hexene, 1-octene, 1-decene, and mixtures thereof; passing said effluent stream from said comonomer synthesis reactor to said downstream gas/liquid phase separator to separate a gas stream from a bottoms stream, wherein said gas stream comprises said one or more comonomers and optionally also ethylene; purifying said bottom stream by removing at least one of solid polymer, catalyst, catalyst activator(s), catalytic decomposition products, purge heavies, and undesirable olefins therefrom; recycling said solvent and/or diluent to said comonomer synthesis reactor; and passing said gas stream to said polyethylene polymerization reactor to provide a comonomer source.

Further, another method for generating 1-hexene, and optionally other desired comonomers immediately before a polyethylene polymerization reactor can include the steps of: providing an in-line comonomer synthesis reactor prior to a polyethylene polymerization reactor, wherein the reactor is a fixed bed type with a catalyst in a fixed position; feeding ethylene to said comonomer synthesis reactor; reacting said ethylene and said catalyst under reaction conditions sufficient to produce an effluent stream comprising one or more comonomers, e.g., selected from the group consisting of 1-hexene, 1-octene, 1-decene, and mixtures thereof; purifying said effluent stream by removing at least one of solid polymer, catalyst, catalyst activator(s), catalytic decomposition products, purge heavies, and undesirable olefins therefrom; and directing said effluent stream to said polyethylene polymerization reactor to provide a comonomer source.

Another method for generating 1-hexene and other desired comonomers immediately before a polyethylene polymerization reactor can include the steps of: providing an in-line comonomer synthesis reactor and a downstream gas/liquid phase separator prior to a polyethylene polymerization reactor; feeding ethylene and a catalyst in a solvent and/or diluent to said comonomer synthesis reactor; reacting said ethylene and said catalyst in said solvent and/or diluent under reaction conditions sufficient to produce an effluent stream comprising ethylene and one or more comonomers, e.g., selected from the group consisting of 1-hexene, 1-octene, 1-decene, and mixtures thereof; passing said effluent stream from said comonomer synthesis reactor to said downstream gas/liquid phase separator to separate a gas stream from a bottom stream, wherein said gas stream comprises a mixture of ethylene and said one or more comonomers; purifying said effluent stream by removing at least one of solid polymer, catalyst, catalyst activator(s), catalytic decomposition products, purge heavies, and undesirable olefins therefrom; and transporting, optionally without isolation or storage, said gas stream to said polyethylene polymerization reactor to provide a comonomer source.

This invention further relates to processes for selectively oligomerizing (e.g., trimerizing and/or tetramerizing) $C_2$ to $C_{12}$ olefins, specifically ethylene, comprising reacting a catalytic composition or compound(s), optionally with one or more activators, with the olefin in the process described herein. As referred to herein, selective oligomerization refers to producing the desired oligomer with a selectivity of the reaction being at least 70%, more specifically at least 80%, by mole of oligomer, with the possibility that an acceptable amount of polymer is present, but with the preference that no polymer is present in the product. In other embodiments, less than 20 wt % of polymer is present, specifically less than 5 wt %, more specifically less than 2 wt %, based upon the total weight of monomer converted to oligomers and polymers, where a polymer is defined to mean a molecule comprising more than 100 mers (repeat units). An "oligomer" as used herein is defined to mean a molecule comprising from 2 to 100 mers (repeat units); however, desired oligomers are defined as described herein, but preferably do not contain more than 20 total carbons and/or preferably do not contain more than 10 repeat units. In other embodiments, selective oligomerization refers to producing one or two desired oligomers, with the selectivity of the one or two desired oligomers summing to at least 80% by sum of total moles of oligomers. Particularly preferred oligomeric olefins are molecules consisting of 2 to 100 mers with the olefinic unsaturation at the end of the oligomer (i.e., alpha-olefin oligomers).

Another aspect of the invention relates to a method for polymerizing a polyethylene copolymer comprising contacting ethylene and one or more of the comonomers made according to any of the methods previously described herein in a polymerization reactor under conditions sufficient to form an ethylene-based polymer. As used herein, an "ethylene-based polymer" is a homopolymer or copolymer in which the relative amount of ethylene repeat units to the total amount of polymerizable monomer repeat units (including ethylene and any other polymerizable monomer repeat units) is more than 50 wt %, preferably more than 70 wt %, for example more than 75 wt %, more than 80 wt %, more than 85 wt %, more than 90 wt %, more than 95 wt %, or more than 99 wt %.

Additionally or alternately, the present invention can include, but is not limited to, embodiments such as those described below:

Embodiment 1. A method for synthesizing a functionalized pyridyl-amine product comprising the following steps:
(a) providing a di-substituted pyridine reactant having the following formula:

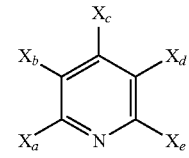

where $X_b$, $X_c$, and $X_d$ are each independently selected from hydrogen and optionally substituted linear, branched, cyclic, heterocyclic, and/or aromatic hydrocarbyl, where at least one of $X_a$ and $X_e$ is a halide, where $X_a$ and $X_e$ can be the same or different, and where, when one of $X_a$ and $X_e$ is not a halide, the one of $X_a$ and $X_e$ that is not a halide is an optionally substituted aryl moiety, preferably provided that the optional substitution(s) on the aryl moeity and on the hydrocarbyl moiety(ies) are not polar substitutions.
(b) selectively activating one of the $X_a$ and $X_e$ halide moieties on the di-substituted pyridine under conditions sufficient to form an activated and substituted pyridine intermediate; and
(c) reacting the activated and substituted pyridine intermediate with one or more other reactants under conditions sufficient to form the functionalized pyridyl-amine product.

Embodiment 2. The method of embodiment 1, wherein the reacting in step (c) occurs in a single reaction step.

Embodiment 3. The method of embodiment 2, wherein the single reaction step (c) occurs by contacting the activated and substituted pyridine with an imine and/or an iminium compound having the following formulas:

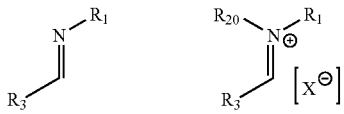

under conditions sufficient to form the functionalized pyridyl-amine product in a single reaction step.

Embodiment 4. The method of any of the previous embodiments, wherein the activated and substituted pyridine intermediate formed in step (b) can be substituted at one of the $X_a$ and $X_e$ positions with an alkali metal and at the other of the $X_a$ and $X_e$ positions with either a halide or an optionally substituted aryl moiety.

Embodiment 5. The method of embodiment 4, wherein the di-substituted pyridine is reacted in step (b) with an alkyl-alkali metal organometallic compound.

Embodiment 6. The method of embodiment 5, wherein the alkyl-alkali metal organometallic compound is butyl-lithium.

Embodiment 7. The method of any of embodiments 4-6, wherein one of $X_a$ and $X_e$ in step (a) is an optionally substituted aryl moiety and the other of $X_a$ and $X_e$ is a halide.

Embodiment 8. The method of embodiment 7, wherein the optionally substituted aryl moiety is an optionally substituted phenyl moiety and wherein the halide is bromine or iodine.

Embodiment 9. The method of embodiment 8, wherein the reacting in step (c) occurs in a single reaction step by contacting the activated and substituted pyridine with an imine and/or an iminium compound having the following formulas:

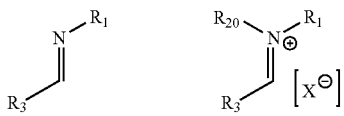

under conditions sufficient to form the functionalized pyridyl-amine product in a single reaction step.

Embodiment 10. The method of embodiment 9, which consists essentially of the two reaction steps (b) and (c).

Embodiment 11. A method for synthesizing a functionalized pyridyl-amine product comprising the following steps:
(a) providing a di-substituted pyridine reactant having the following formula:

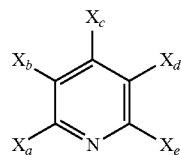

where $X_b$, $X_c$, and $X_d$ are each independently selected from hydrogen and optionally substituted linear, branched, cyclic, heterocyclic, and/or aromatic hydrocarbyl, preferably provided that any of the optional substitutions on the hydrocarbyl moiety(ies) are not polar substitutions, and where both of $X_a$ and $X_e$ are halides.

(b) selectively activating one of the $X_a$ and $X_e$ halide moieties on the di-substituted pyridine under conditions sufficient to form a mono-metallated, halo-substituted pyridine intermediate;
(c) reacting the mono-metallated, halo-substituted pyridine intermediate with one or more other reactants under conditions sufficient to form a halo-substituted pyridinyl aldehyde intermediate;
(d) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate; and
(e) aminating the (optionally substituted aryl)-substituted pyridinyl aldehyde intermediate by contacting it with one or more other reactants under conditions sufficient to form the functionalized pyridyl-amine product.

Embodiment 12. The method of embodiment 11, wherein the di-substituted pyridine is selectively activated in step (b) by contacting it with a hydrocarbyl-mixed metal organometallic compound having a hydrocarbyl portion and a mixed metal portion.

Embodiment 13. The method of embodiment 12, wherein the hydrocarbyl-mixed metal organometallic compound selectively converts one of the $X_a$ and $X_e$ halide moieties to a metal-containing moiety.

Embodiment 14. The method of embodiment 13, wherein the mixed metal portion comprises at least one alkali metal and at least one divalent or trivalent metal.

Embodiment 15. The method of embodiment 14, wherein the at least one alkali metal comprises lithium and wherein the at least one divalent or trivalent metal comprises at least one of beryllium, magnesium, calcium, boron, and aluminum.

Embodiment 16. The method of any of embodiments 11-15, wherein the conditions sufficient for selective activation in step (b) comprise a temperature above −78° C.

Embodiment 17. The method of embodiment 16, wherein the temperature is above −25° C.

Embodiment 18
The method of embodiment 16, wherein the temperature is between −20° C. and 0° C.

Embodiment 19. The method of any of embodiments 11-18, wherein the aminating step (e) can be accomplished in two distinct reaction steps, as follows:
(e1) reacting the (optionally substituted aryl)-substituted pyridinyl aldehyde intermediate with a substituted amine having the formula $(R_1)(R_{20})NH$ under conditions sufficient to form a pyridyl-amine/pyridyl-iminium intermediate;
(e2) reacting the pyridyl-amine/pyridyl-iminium intermediate with a metal hydrocarbyl compound under conditions sufficient to form the functionalized pyridyl-amine product.

Embodiment 20. A method for forming an olefin oligomer using a pyridylamine-containing catalytic composition, comprising the steps of:
(a) synthesizing, and optionally purifying, a functionalized pyridyl-amine product according to the method of claim 1;
(b) forming a metal-ligand precursor by contacting the pyridyl-amine product with a metal precursor compound, and optionally also with an activator;
(c) contacting an olefin feed with said metal-ligand precursor under reaction conditions sufficient to produce an effluent comprising a trimerized and/or tetramerized olefin product; and
(d) optionally isolating and/or purifying the trimerized and/or tetramerized olefin product.

Embodiment 21. The method of embodiment 20, wherein the metal in the metal precursor compound comprises one or more elements from Groups 4-10 of the Periodic Table of Elements.

Embodiment 22. The method of embodiment 21, wherein the metal in the metal precursor compound comprises chromium.

Embodiment 23. A method for polymerizing an ethylene-based polymer comprising:
forming an olefin oligomer using a pyridylamine-containing catalytic composition according to the method of claim 20 to provide one or more polymerizable comonomers from the trimerized and/or tetramerized olefin product; and
contacting ethylene and the one or more polymerizable comonomers with a polymerization catalyst in a polymerization reactor under conditions sufficient to form the ethylene-based polymer.

Embodiment 24. The method of embodiment 23, wherein the ethylene-based polymer comprises more than 80 wt % ethylene, based on the total amount of polymerizable monomer repeat units.

Embodiment 25. A method for synthesizing a purified functionalized pyridyl-amine product comprising the following steps:
(a) providing a di-substituted pyridine reactant having the following formula:

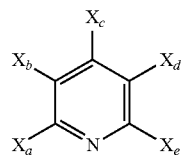

where $X_b$, $X_c$, and $X_d$ are each independently selected from hydrogen and optionally substituted linear, branched, cyclic, heterocyclic, and/or aromatic hydrocarbyl, preferably provided that any of the optional substitutions on the hydrocarbyl moiety(ies) are not polar substitutions, and where both of $X_a$ and $X_e$ are halides.
(b) selectively activating one of the $X_a$ and $X_e$ halide moieties on the di-substituted pyridine under conditions sufficient to form a mono-metallated, halo-substituted pyridine intermediate;
(c) reacting the mono-metallated, halo-substituted pyridine intermediate with one or more other reactants under conditions sufficient to form a halo-substituted pyridinyl aldehyde intermediate;
(d) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate;
(e) aminating the (optionally substituted aryl)-substituted pyridinyl aldehyde intermediate by contacting it with one or more other reactants under conditions sufficient to form the crude functionalized pyridyl-amine product;
(f) treating the crude functionalized pyridyl-amine product with an acid to form a functionalized pyridyl-ammonium product salt;
(g) triturating the functionalized pyridyl-ammonium product salt to remove impurities; and
(h) treating the isolated, functionalized pyridyl-ammonium product salt with a base to form a purified functionalized pyridyl-amine product.

EXAMPLES

The following Examples and Comparative Examples are merely illustrative of one or more aspects of the invention described herein and were not included to limit in any way the scope of the invention, as recited in the claims below. All air sensitive procedures were performed under a purified argon or nitrogen atmosphere in a Vacuum Atmospheres or MBraun glove box. All solvents used were anhydrous, de-oxygenated and purified according to known techniques [see, for example, D. D. Perrin & W. L. F. Armarego, *Purification of Laboratory Chemicals*, 3$^{rd}$ Ed., (Pergamon Press: New York, 1988)]. All ligands were prepared according to procedures known to those of skill in the art, e.g., under inert atmosphere conditions, etc.

Comparative Example 1

The pyridyl-amine ligands in this Comparative Example can be prepared according to the procedures known to those of ordinary skill in the art, for example, as described in U.S. Patent Application Publication No. 2006/0247403, which is herein incorporated by reference in its entirety, and U.S. Pat. Nos. 6,750,345 and 6,713,577, and illustrated by the reaction scheme given in Scheme 1, where X is a halogen, where $R^1$ is selected from the group consisting of hydrogen, optionally substituted hydrocarbyl, and heteroatom-containing hydrocarbyl (e.g., hydrogen, optionally substituted alkyl, heteroalkyl, cycloalkyl, heterocycloalkyl, aryl, heteroaryl, and combinations thereof, such as a ring having from 4-8 atoms therein selected from the group consisting of substituted cycloalkyl, heterocycloalkyl, aryl, and heteroaryl), and where $R_2$, $R_4$, $R_5$, $R_6$, and $R_7$ are independently selected from the group consisting of hydrogen, halogen, nitro, and optionally substituted alkyl, heteroalkyl, aryl, heteroaryl, alkoxy, aryloxy, amino, and combinations thereof, wherein optionally two or more $R_1$, $R_2$, $R_4$, $R_5$, $R_6$, and $R_7$ groups may be joined to form one or more optionally substituted ring systems.

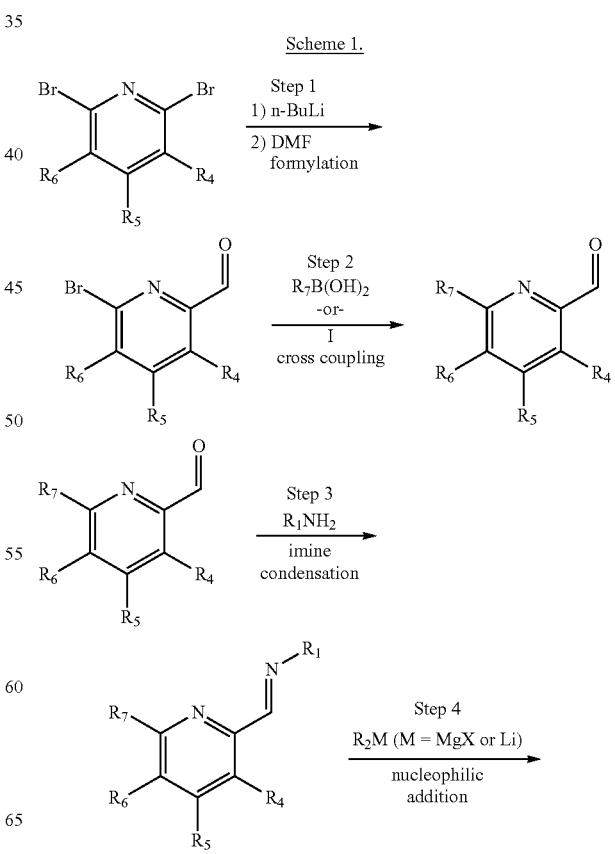

Scheme 1.

-continued

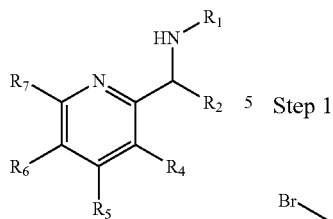

The reaction to produce a pyridyl-amine ligand can be performed in four general reaction steps. In step 1, a bromopyridine can be reacted with n-butyl lithium (n-BuLi) and DMF in a formylation reaction, replacing a bromide atom on the bromopyridine with an aldehyde group. The remaining bromide atom on the initial bromopyridine molecule can then be replaced with $R_7$ through a coupling reaction. The third reaction step is an imine-forming condensation reaction. The imine condensation reaction is followed by reaction step 4, the nucleophilic addition of $R_2$ to the structure.

Generally, $R_2M$ is a nucleophile such as an alkylating, arylating, or hydrogenating reagent and M is a metal such as a main group metal, or a metalloid such as boron. The alkylating, arylating, or hydrogenating reagent may be a Grignard, alkyl- or aryl-lithium, or borohydride reagent. In step 4, a complexing agent such as magnesium bromide can be used to direct the nucleophile selectively to the imine carbon, as described in U.S. Pat. Nos. 6,750,345 and 6,713,577.

Comparative Example 2

Alternative strategies to the reaction scheme illustrated in Scheme 1 can also be employed in this Comparative Example from U.S. Patent Application Publication No. 2006/0247403. For example, in Scheme 2, ligands where $R_{20}$ is selected from the same group as $R_1$ but is not hydrogen, may be synthesized through a condensation of the aldehyde with a secondary amine ($R_1R_{20}NH$), using benzotriazole to create a stabilized iminium salt. Nucleophilic addition of $R_2$ to the imine follows, releasing the benzotriazole adduct. An example of each type of pyridyl-amine ligand synthesis ($R_{20}$=hydrogen, $R_{20}$=alkyl) is given in Comparative Examples 3 (a and b) and 4, respectively, below.

Comparative Example 3a $R_{20}$=Hydrogen

Step 1

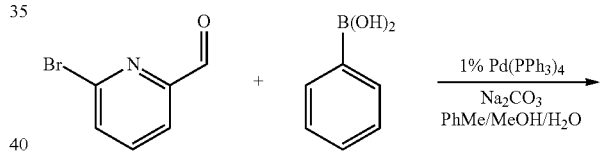

To a solution of 23.7 g (100 mmol) of 2,6-dibromopyridine in 150 mL of anhydrous, degassed THF cooled to −78° C. was added dropwise under $N_2$ a solution of 11.0 mL (110 mmol) of 10.0 M n-BuLi in 150 mL anhydrous, degassed $Et_2O$. After 2 hours at −78° C., 24.2 mL (300 mmol) of anhydrous degassed DMF was added dropwise with rapid stirring. This solution was stirred at −78° C. for 2 hours, and was then allowed to warm to room temperature (RT) overnight. The solution was cooled to −78° C. and 100 mL of 1.0 M aq. HCl was added slowly. The organic phase was separated and the aqueous phase was washed with 3×50 mL $Et_2O$. The organic washes were combined and washed with 3×50 mL $H_2O$ and 3×50 mL brine, then dried over $Na_2SO_4$. The volatiles were removed in vacuo to provide an orange oil. The oil was triturated with hexanes to give 2-bromo-6-formylpyridine as a pale orange solid that was washed with cold pentanes and dried under vacuum overnight.

Step 2

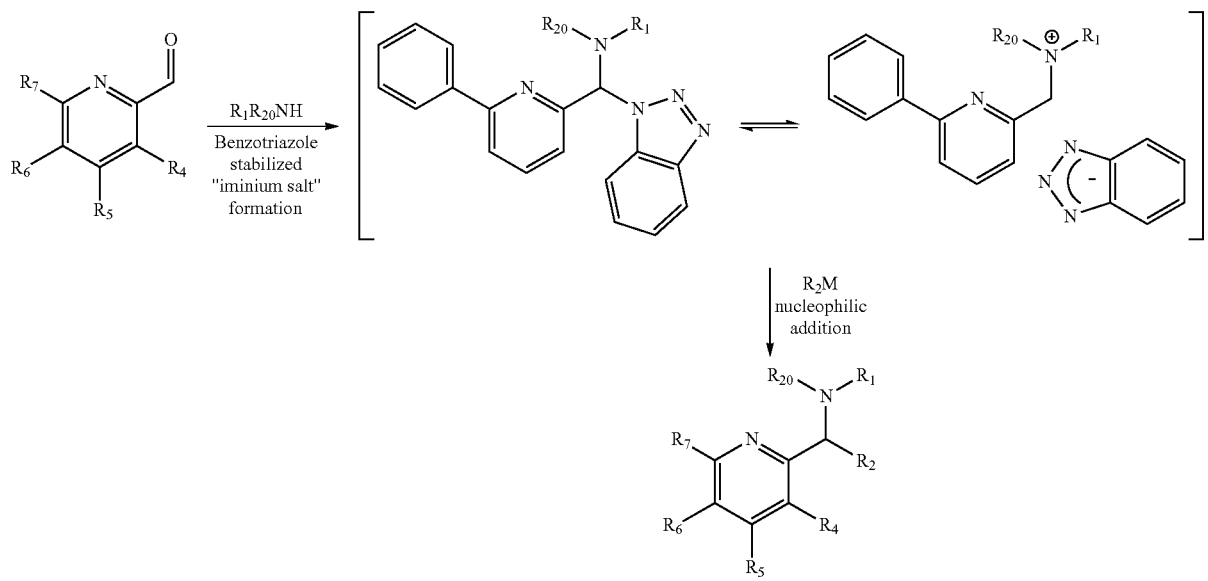

Scheme 2.

-continued

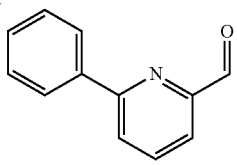

Phenylboronic acid (1.46 g, 12 mmol) and Na₂CO₃ (2.65 g, 25 mmol) were dissolved in 60 mL of degassed 4:1 H₂O/MeOH. This solution was added via cannula to a solution of 1.86 g (10 mmol) of 2-bromo-6-formylpyridine and 116 mg (0.10 mmol) of Pd(PPh₃)₄ in 50 mL of degassed toluene. The biphasic mixture was vigorously stirred and heated at 70° C. under N₂ for 4 h. On cooling to RT, the organic phase was separated and the aqueous phase was washed with 3×25 mL of Et₂O. The combined organic extracts were washed with 3×25 mL of H₂O and 20 mL of brine and dried over Na₂SO₄. After removing the volatiles in vacuo, the resultant brown oil was chromatographed on silica with hexanes/CH₂Cl₂. Clean fractions were combined and the volatiles were removed to provide 2-formyl-6-phenylpyridine as a white solid.

Step 3

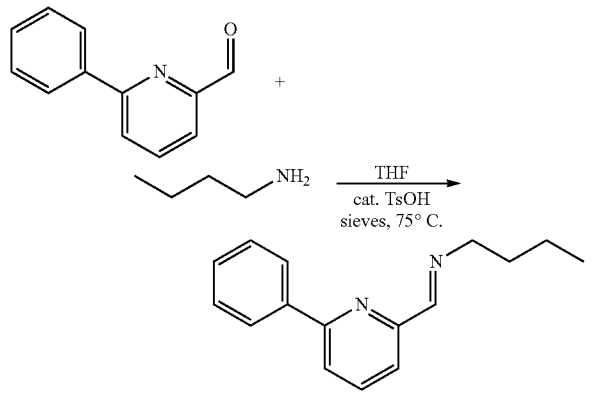

A solution of 916 mg (5 mmol) of 2-formyl-6-phenylpyridine and 402 mg (5.5 mmol) of n-butylamine in 50 mL of anhydrous THF containing 3 Å sieves and a catalytic amount of TsOH, was heated at 75° C. under N₂ for 8 h. Filtration and removal of the volatiles in vacuo provided 6-phenylpyridine-2-(n-butyl)-imine as a yellow oil, which was used directly in subsequent nucleophilic reactions without purification.

Step 4

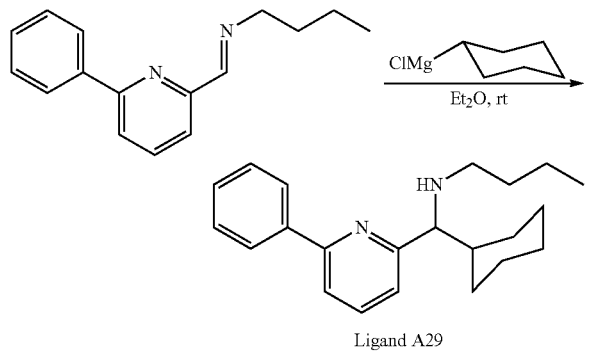

Ligand A29

To a vigorously-stirred solution of 6-phenylpyridine-2-(n-butyl)-imine (300 mg, 1 mmol) in 2 mL of Et₂O under N₂, a solution of cyclohexylmagnesium chloride (600 µL of 2 M in Et₂O, 1.2 mmol) was added. After stirring at RT for 12 h, the reaction was quenched with aq. NH₄Cl. The organic layer was separated, washed with brine and H₂O, then was dried over Na₂SO₄. Following chromatography (alumina gel, 10% ethyl acetate/hexanes), the product was isolated as a yellow oil. The use of MgBr₂ as a complexing reagent can aid in the selectivity of Step 4, as described in U.S. Pat. Nos. 6,750,345 and 6,713,577. For certain pyridyl-amine ligands, the use of a complexing reagent is not necessary. In some cases the regioselectivity of Step 4 is such that the products of nucleophilic attack at both the imine carbon and the imine nitrogen can be isolated, e.g., ligands such as A29 can be obtained from the same reaction, with the product ratio depending on the conditions used.

Comparative Example 3b

R₂₀=Hydrogen

Step 1

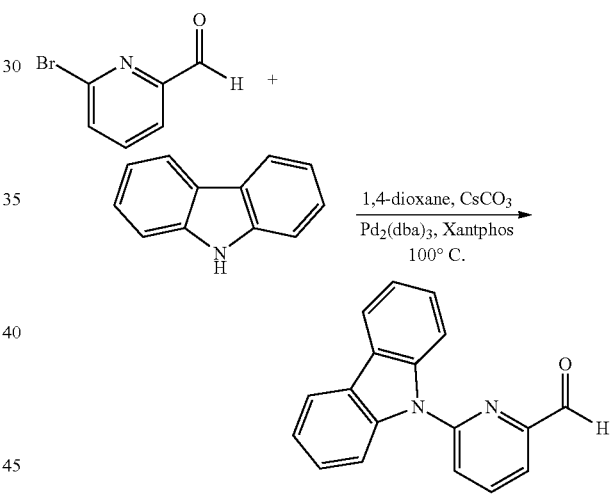

6-Bromopyridine-2-carboxaldehyde (1.86 g, 10.0 mmol) and carbazole (1.84 g, 11 mmol) were combined in anhydrous 1,4-dioxane (40 mL) under inert atmosphere. Cesium carbonate (4.56 g, 14 mmol), xantphos (0.382 mg, 0.66 mmol) and Pd₂(dba)₃ (0.275 g, 0.3 mmol) were added to the reaction mixture. The reaction mixture was sealed and heated at 100° C. for 72 h. The reaction was then cooled to ambient temperature, diluted with EtOAc (150 mL) and was washed with brine (75 mL). The organic layer was separated and dried over Na₂SO₄. The mixture was filtered, and the material was adsorbed onto neutral alumina for alumina chromatography. The material was eluted using a gradient of 0-20% EtOAc in hexanes. Fractions containing the product were pooled and evaporated yielding a product mixture as a yellow solid (2.28 g). GC-MS and ¹H NMR confirmed this mixture included the desired product and the starting carbazole. The material was carried on without further purification.

Step 2

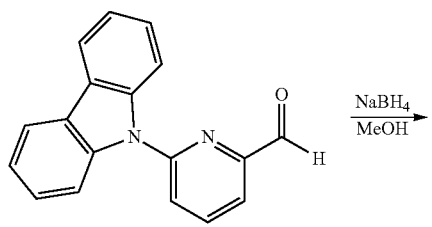

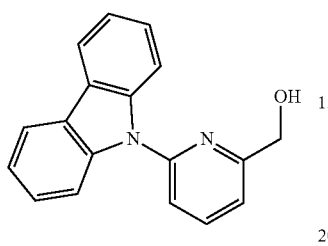

The product mixture described above (1.50 g) was taken up with stirring in methanol (12 mL). The resulting solution was cooled to 0° C. Sodium borohydride (0.313 g, 8.27 mmol) was added cautiously. The resulting mixture was stirred at 0° C. for 15 min. The reaction was heated at 80° C. for 1 h. The mixture was then poured into a brine solution (50 mL) and extracted with EtOAc (3×50 mL). The extracts were combined and dried over Na₂SO₄. The solution was filtered and adsorbed onto alumina gel for chromatography on neutral alumina. The material was eluted using a gradient of 0-20% EtOAc in hexanes. The product was obtained after evaporation of the eluent as a colorless foam (0.965 g).

Step 3

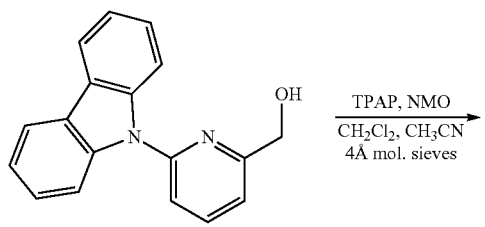

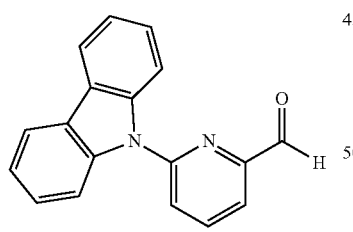

The 6-carbazolyl-2-hydroxymethylpyridine (0.965 g, 3.52 mmol) was dissolved in dichloromethane (35 mL) and acetonitrile (7 mL). N-methylmorpholine-N-oxide (0.619 g, 5.28 mmol) was added to the stirring solution followed by activated 4 Å-molecular sieves (2 g). The resulting mixture was stirred at ambient temperature for 15 min. Tetra-N-propylammonium-perruthenate (62 mg, 0.176 mmol) was then added in one portion, and the resulting mixture was stirred at ambient temperature for 38 h. The reaction was then quenched by addition of an aqueous 20% solution of sodium thiosulfate (10 mL). The organic layer was separated and the aqueous layer was extracted with CH₂Cl₂ (3×50 mL). The organic layer and extracts were combined and dried over Na₂SO₄. The material was adsorbed onto alumina gel for alumina chromatography. The material was eluted using a gradient of 0-20% diethyl ether in hexane. The product was obtained after evaporation of the eluent as a white solid (0.425 g).

Step 4

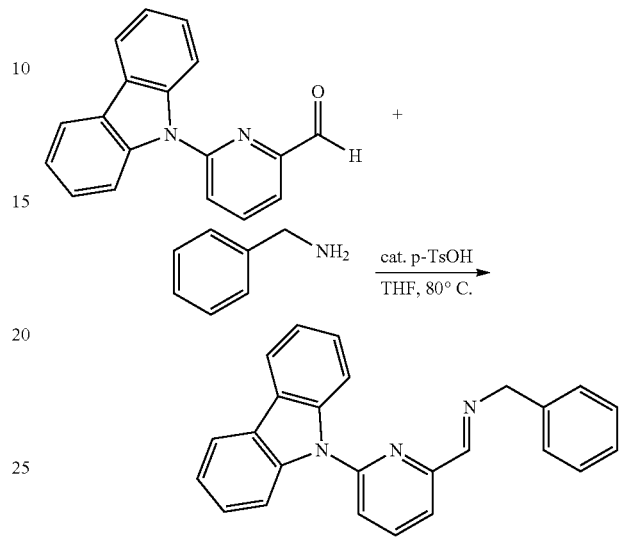

The 6-carbazolylpyridine-2-carboxaldehyde (0.358 g, 1.31 mmol) was taken up in anhydrous THF (16 mL). Benzylamine (0.154 g, 1.44 mmol), p-TsOH.H₂O (30 mg, 0.158 mmol) and 4 Å-molecular sieves (2 g) were added to the stirring mixture. The reaction vessel was sealed and heated at 80° C. for 30 min. The reaction mixture was cooled to ambient temperature, diluted with EtOAc (50 mL) and filtered to remove the sieves. The resulting solution was washed with an aqueous 1.5 M KHCO₃ solution (30 mL). The organic layer was separated and dried over Na₂SO₄. The material was filtered, and the volatile materials were removed to yield the desired product as a white solid (0.425 g).

Step 5

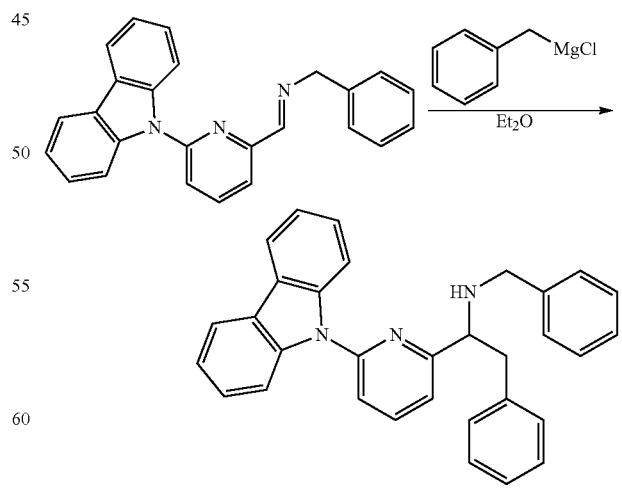

Ligand A51

The benzyl imine (0.425 g, 1.18 mmol) was taken up in anhydrous diethyl ether (10 mL). Benzylmagnesium chloride solution in diethyl ether (1.30 mL, 1.3 mmol) was added dropwise to the stirring solution. The resulting reaction mixture was stirred at ambient temperature for 1 h. The reaction mixture was then quenched by addition of brine (20 mL). The resulting mixture was extracted with EtOAc (3×50 mL). The organic extracts were combined and dried over $Na_2SO_4$. The solution was filtered, and the material was adsorbed onto alumina gel for alumina chromatography. The material was eluted using 50% diethyl ether in hexanes as the eluent. The product was obtained in this manner as a yellow solid (0.377 g).

Ligands illustrated in FIGS. 1, 2, 3, 4, and 5 of U.S. Patent Application Publication No. 2006/0247403 were prepared using the procedures detailed above and/or therein, or through variations to these procedures that are apparent to one of ordinary skill in the art.

Comparative Example 4

$R_{20}$=Alkyl

Step 1

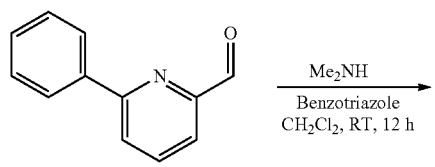

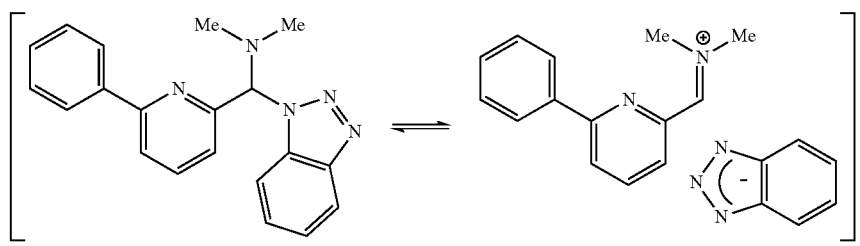

2-Formyl-6-phenylpyridine, 200 mg (1.10 mmol), and 130 mg (1.10 mmol) of benzotriazole were dissolved in 10 mL of anhydrous $CH_2Cl_2$ containing approximately 100 mg of $MgSO_4$ as a drying agent. Dimethylamine (0.61 mL of a 2M hexanes solution, 1.2 mmol) was added at ambient temperature. The mixture was vigorously stirred at ambient temperature for 12 h, then filtered to remove inorganic solids. The volatiles were removed in vacuo and the resultant yellow foam was used directly in subsequent nucleophilic reactions without purification.

Step 2

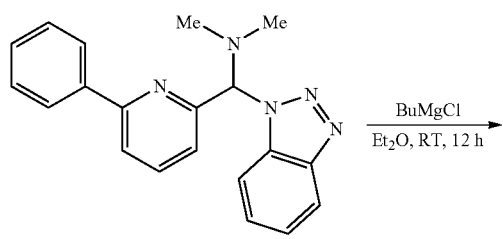

-continued

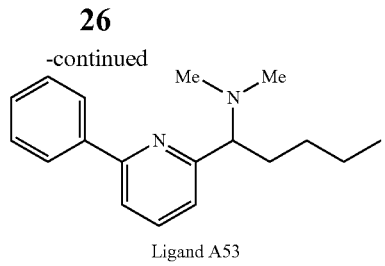

Ligand A53

To a vigorously-stirred solution of the crude 6-phenylpyridine-2-(dimethylamino)-benzotriazole iminium salt (330 mg, 1 mmol) in 2 mL of $Et_2O$ under $N_2$, a solution of butylmagnesium chloride (550 μL of 2 M in $Et_2O$, 1.1 mmol) was added. After stirring at RT for 12 h, the reaction was quenched with aq. $NH_4Cl$. The organic layer was separated, washed with brine and $H_2O$, then was dried over $Na_2SO_4$. Following chromatography (alumina gel, 10% ethyl acetate/hexanes), the product was isolated as a yellow oil.

Example 1

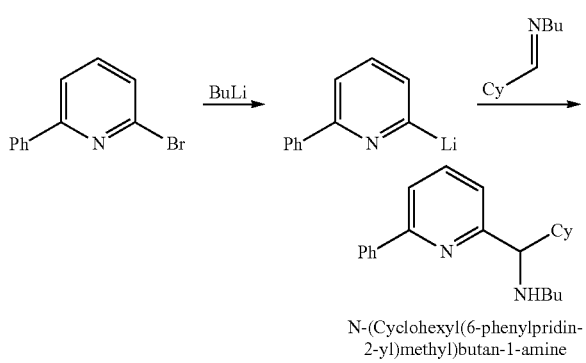

N-(Cyclohexyl(6-phenylpridin-2-yl)methyl)butan-1-amine

Example 1 describes an alternate synthesis scheme to make the same ligand product as made in Comparative Example 3a. In this Example, Cy is an abbreviation for "cyclohexyl." In the method of Example 1, $Et_2O$ (35 mL) was added to 2-bromo-6-phenylpyridine (1.205 g, 5.15 mmol) to form a clear colorless solution. At −4° C., a hexane solution of BuLi (2.18 mL, 5.15 mmol) was added dropwise. The resulting clear orange solution was stirred for 5 minutes, and then N-(cyclohexylmethylene)butan-1-amine (0.904 g, 5.40 mmol) was added in one portion. The mixture was warmed to ambient temperature and stirred for 10 minutes. Water (1 mL) was then added. The volatiles were removed under reduced pressure and the residue was extracted with $Et_2O$ (10 mL) and filtered. The $Et_2O$ extract was dried over $Na_2SO_4$. Removal of the volatiles afforded 1.77 g of the crude product that $^1H$ NMR analysis indicated was >90% pure, with the major impurity being 2-phenylpyridine. This crude product was purified by flash chromatography on a $SiO_2$ column. The impurities were first eluted with $CH_2Cl_2$ and the product was then eluted using EtOAc. Yield: 1.45 g (87.3%). $^1H$ NMR($C_6D_6$): δ 8.11-8.17 (2H, m), 7.12-7.30 (5H, m), 6.96 (1H, 6H, dd, J=1.3, 7.1 Hz), 3.53 (1H, d, J=6.9 Hz), 2.47 (2H, m), 2.22 (1H, br m), 1.05-1.85 (15H, br m), 0.82 (3H, t, J=7.2 Hz).

Example 2

Example 2 describes an alternate synthesis scheme to make the same ligand product as made in Comparative Example 4.

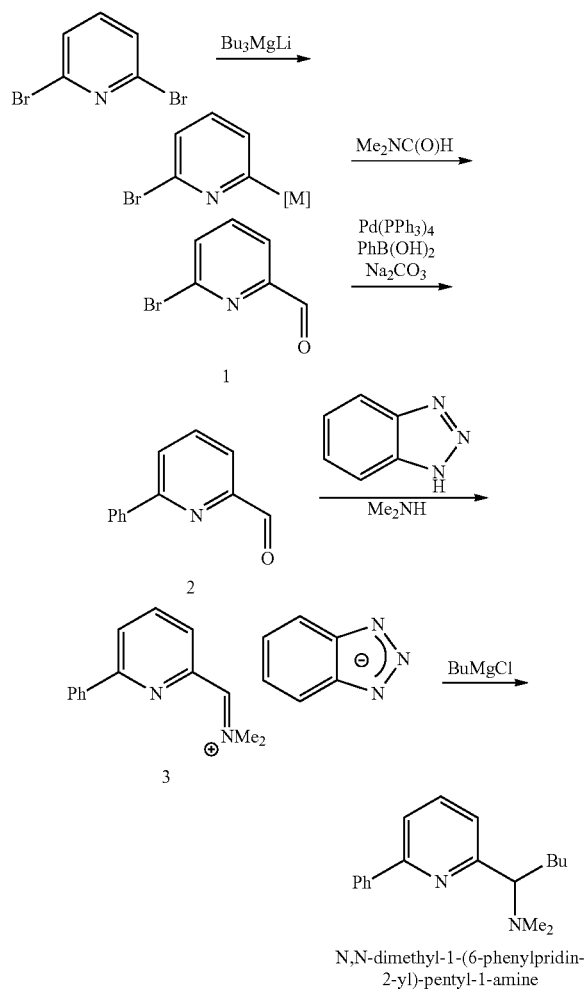

Step 1—Preparation of Intermediate 1

To a 12 L flask equipped with a mechanical stirrer, addition funnel, nitrogen inlet, and thermowell was added BuLi (619 mL, 1.55 mol). To this solution was added dry toluene (750 mL). This solution was cooled to −15° C. in an ice/MeOH bath. To this solution was added BuMgCl (387 mL, 0.774 mol) over 30-45 mins so that the temperature did not exceed 0° C. during the addition. A fine white to gray suspension formed. This was stirred for 30 mins at −15° C. During this time 2,6-dibromopyridine (500 g, 2.11 mol) was dissolved in dry toluene (3 L) with some slight external heating. After the stir time the solution of 2,6-dibromopyridine was charged to an addition funnel and slowly added to the reaction flask at a rate that the temperature did not exceed −5° C. (ca. 1.5 h). Once the addition of the pyridine was complete the mixture was stirred for 45 mins. Then an aliquot was taken and quenched into 20% aqueous citric acid to determine the extent of metal exchange by $^1H$ NMR and TLC (25% EtOAc/heptane). A second 12 L flask equipped with a mechanical stirrer, nitrogen inlet, and thermowell was charged with toluene (750 mL) and dimethylformamide (250 mL) and cooled to −15° C. in an ice/MeOH bath. The contents of the initial reaction flask were transferred via cannula to the toluene/DMF solution at a rate that the temperature did not exceed 5° C. The reaction was stirred for 45 mins and determined to be complete. The contents of the reaction flask were transferred into a separatory funnel charged with 4 L water and citric acid (1 kg). The mixture was stirred for 15 mins, layers separated. The organic layer was washed with water (4 L), then saturated NaCl solution (4 L), then dried over $Na_2SO_4$ and solvent removed under reduced pressure to yield an off white to yellow solid of intermediate 1 (355.7 g, 90%).

Step 2—Preparation of Intermediate 2

A 22 L flask equipped with a mechanical stirrer, reflux condenser, thermowell, and nitrogen inlet was charged with water (4.8 L), MeOH (1.2 L), and $Na_2CO_3$ (800 g, 7.55 mol). This mixture was stirred until all the $Na_2CO_3$ was dissolved and then $PhB(OH)_2$ (553 g, 4.53 mol) was added. To this mixture was added a solution of 1 (560 g, 3.02 mol) in toluene (6 L). This mixture was sparged with nitrogen for 20 min and then $(Ph_3P)_4Pd$ (35 g, 0.0274 mol) was added and the reaction was heated to reflux for 2 hrs. HPLC of an aliquot showed that the reaction was complete, and the external heating was removed. The reaction mixture was cooled overnight and then poured into 8 L of stirring water. This mixture was stirred for 20 mins until all solids were dissolved. The layers were separated, and the organic layer was washed with brine (4 L), dried over $Na_2SO_4$, and the solvent removed under reduced pressure. The residue was purified by Kugelrohr distillation (115° C., 0.1-0.2 mTorr) to give a pale yellow oil which solidified upon standing (502.3 g, 91%).

Step 3—Preparation of Intermediate 3

To a 22 L flask equipped with a nitrogen inlet, reflux condenser, thermowell, and mechanical stirrer was charged 2 (668 g, 3.65 mol), $CH_2Cl_2$ (8 L), and $MgSO_4$ (350 g). To this mixture was added benzenetriazole (435 g, 3.65 mol) with an endotherm of about 8° C. down to 17° C. To this mixture was added $Me_2NH$ (2 L, 2M in THF, 4 mol) via an addition funnel in a rapid fashion. The reaction released an exotherm up to 30° C. and then cooled back to ambient temperature overnight. The mixture was filtered through a pad of Celite and the solvents were removed under reduced pressure to give a waxy yellow residue. This material was taken on to the next step without purification.

Step 4—Preparation of N,N-dimethyl-1-(6-phenylpyridin-2-yl)-pentyl-1-amine

To a 22 L flask equipped with a mechanical stirrer, addition funnel, nitrogen inlet, and thermowell was charged 3 (assuming 3.65 mol from previous reaction) and $Et_2O$ (10 L). The reaction was cooled to 15° C. with an acetone bath cooled by adding dry ice intermittently. To this solution was added BuMgCl solution (2 L, 4 mol) at a rate that the temperature did not exceed 17° C. (controlled by rate of addition and by addition of dry ice to the cold bath, about 30 mins addition time). Solids began to form immediately on addition. This suspension was stirred for 30 mins and checked for completion. Upon completion, the reaction was quenched into aqueous saturated $NH_4Cl$ (about 6 L) and stirred for 20 mins. The layers were separated and the organic was washed with 10% $Na_2CO_3$ solution (2×6 L), brine (4 L), dried over $Na_2SO_4$, and the solvent removed under reduced pressure to give an orange/red oil (960 g).

The oil was split into 2×22 L reaction flasks (480 g each) and dissolved in methyl t-butyl ether (MTBE) (10 L). The solution was heated to reflux, and a solution of maleic acid (212 g, 1.82 mol) in MTBE (4 L) was slowly added. Solids began to form almost immediately. The suspension was stirred for 2 h at reflux, and then the heat was turned off and the reaction slowly cooled to ambient temperature overnight. The mixture was filtered, and the solids were washed with MTBE (4 L) and dried on the filter pad. The pinkish maleic acid salt was added to a separatory funnel containing 10 L of MTBE and 10 L of water. To this mixture was added NaOH solution (24% w/v, about 1.1 L) slowly checking the pH of the aqueous intermittently. Once the pH was about 10 (a color change of the organic is an indicator of the pH), the mixture was stirred for 30 mins, the layers separated and the organic washed with brine, dried over $Na_2SO_4$ and the solvent removed under reduced pressure to afford the product as a yellow/orange oil (818 g, 83% from 2). $^1H$ NMR ($CDCl_3$): δ 8.04 (2H, d), 7.70 (1H, t), 7.61 (1H, d), 7.50-7.37 (3H, m), 7.17 (1H, d), 3.55-3.50 (1H, m), 2.29 (6H, s), 2.02-1.85 (2H, m), 1.40-1.05 (4H, m), 0.84 (3H, t). $^{13}C\{^1H\}$ NMR ($CDCl_3$): δ 160.7, 156.3, 140.0, 136.7, 129.0, 128.9, 127.2, 121.8, 118.7, 71.5, 42.8, 31.9, 28.8, 23.1, 14.3.

Example 3

Example 3 describes another alternate synthesis scheme to make the same ligand product as made in Comparative Example 4.

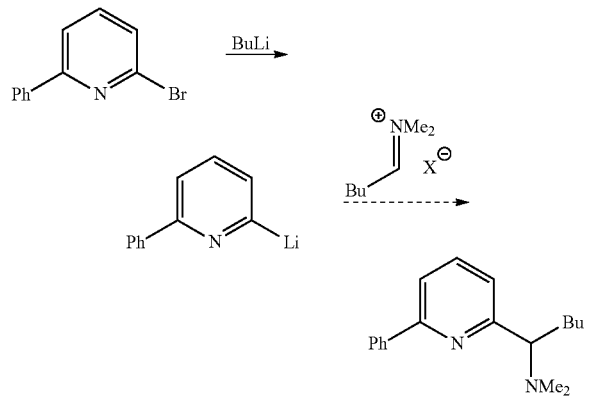

$Et_2O$ is added to 2-bromo-6-phenylpyridine to form a clear colorless solution. At −4° C., a hexane solution of BuLi (1 equiv) is added dropwise. The resulting clear orange solution is stirred for 5 minutes, and then is cooled to −78° C. Then N-methyl-N-pentylidenemethanaminium iodide (1 equiv) is added, and the mixture is slowly warmed to ambient temperature. After stirring overnight, the volatiles are removed, and the residue is extracted with hexane and is filtered. Removal of the volatiles affords the product. Characterization data are believed to be the same as those given after Step 4 of Example 2.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A method for forming an olefin oligomer using a pyridylamine-containing catalytic composition, comprising the steps of:
   (a) synthesizing, and optionally purifying, a functionalized pyridyl-amine product by:
      (i) providing a di-substituted pyridine reactant having the following formula:

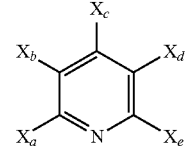

where $X_b$, $X_c$, and $X_d$ are each independently selected from hydrogen and optionally substituted linear, branched, cyclic, heterocyclic, and/or aromatic hydrocarbyl, where at least one of $X_a$ and $X_e$ is a halide, where $X_a$ and $X_e$ can be the same or different, and where, when one of $X_a$ and $X_e$ is not a halide, the one of $X_a$ and $X_e$ that is not a halide is an optionally substituted aryl moiety;

(ii) selectively activating one of the $X_a$ and $X_e$ halide moieties on the di-substituted pyridine under conditions sufficient to form an activated and substituted pyridine intermediate; and
      (iii) reacting the activated and substituted pyridine intermediate with one or more other reactants, said one or more other reactants including an imine and/or an iminium compound having the following formulas:

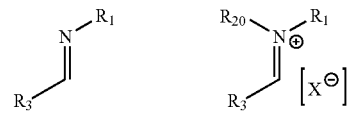

under conditions sufficient to form the functionalized pyridyl-amine product in a single reaction step;
   (b) forming a metal-ligand precursor by contacting the pyridyl-amine product with a metal precursor compound, and optionally also with an activator;

(c) contacting an olefin feed with said metal-ligand precursor under reaction conditions sufficient to produce an effluent comprising a trimerized and/or tetramerized olefin product; and (d) optionally isolating and/or purifying the trimerized and/or tetramerized olefin product.

2. The method of claim 1, wherein the metal in the metal precursor compound comprises one or more elements from Groups 4-10 of the Periodic Table of Elements.

3. The method of claim 1, wherein the reacting in (iii) occurs in a single reaction step.

4. The method of claim 1, wherein the activated and substituted pyridine intermediate formed in (ii) can be substituted at one of the $X_a$ and $X_e$ positions with an alkali metal and at the other of the $X_a$ and $X_e$ positions with either a halide or an optionally substituted aryl moiety.

5. The method of claim 4, wherein the di-substituted pyridine is reacted in (ii) with an alkyl-alkali metal organometallic compound.

6. A method for forming an olefin oligomer using a pyridylamine-containing catalytic composition, comprising the steps of:
(a) synthesizing a functionalized pyridyl-amine product by:
(i) providing a di-substituted pyridine reactant having the following formula:

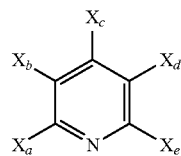

where $X_b$, $X_c$, and $X_d$ are each independently selected from hydrogen and optionally substituted linear, branched, cyclic, heterocyclic, and/or aromatic hydrocarbyl, and where both of $X_a$ and $X_e$ are halides;
(ii) selectively activating one of the $X_a$ and $X_e$ halide moieties on the di-substituted pyridine under conditions sufficient to form a mono-metallated, halo-substituted pyridine intermediate by contacting it with a hydrocarbyl-mixed metal organometallic compound having a hydrocarbyl portion and a mixed metal portion;
(iii) reacting the mono-metallated, halo-substituted pyridine intermediate with one or more other reactants under conditions sufficient to form a halo-substituted pyridinyl aldehyde intermediate;
(iv) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate; and
(v) aminating the (optionally substituted aryl)-substituted pyridinyl aldehyde intermediate by contacting it with one or more other reactants under conditions sufficient to form the functionalized pyridyl-amine product;
(b) forming a metal-ligand precursor by contacting the pyridyl-amine product with a metal precursor compound, and optionally also with an activator;
(c) contacting an olefin feed with said metal-ligand precursor under reaction conditions sufficient to produce an effluent comprising a trimerized and/or tetramerized olefin product; and
(d) optionally isolating and/or purifying the trimerized and/or tetramerized olefin product.

7. The method of claim 6, wherein the hydrocarbyl-mixed metal organometallic compound selectively converts one of the $X_a$ and $X_e$ halide moieties to a metal-containing moiety.

8. The method of claim 7, wherein the mixed metal portion comprises at least one alkali metal and at least one divalent or trivalent metal.

9. The method of claim 8, wherein the at least one alkali metal comprises lithium and wherein the at least one divalent or trivalent metal comprises at least one of beryllium, magnesium, calcium, boron, and aluminum.

10. The method of claim 6, wherein the conditions sufficient for selective activation in (ii) comprise a temperature above −78° C.

11. The method of claim 10, wherein the temperature is between −20° C. and 0° C.

12. The method of claim 6, wherein the aminating in (v) can be accomplished in two distinct reaction steps, as follows:
(e1) reacting the (optionally substituted aryl)-substituted pyridinyl aldehyde intermediate with a substituted amine having the formula $(R_1)(R_{20})NH$ under conditions sufficient to form a pyridyl-amine/pyridyl-iminium intermediate; and
(e2) reacting the pyridyl-amine/pyridyl-iminium intermediate with a metal hydrocarbyl compound under conditions sufficient to form the functionalized pyridyl-amine product.

13. The method of claim 6, wherein the metal in the metal precursor compound comprises one or more elements from Groups 4-10 of the Periodic Table of Elements.

14. A method for forming an olefin oligomer using a pyridylamine-containing catalytic composition, comprising the steps of:
(a) synthesizing a functionalized pyridyl-amine product by:
(i) providing a di-substituted pyridine reactant having the following formula:

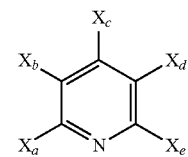

where $X_b$, $X_c$, and $X_d$ are each independently selected from hydrogen and optionally substituted linear, branched, cyclic, heterocyclic, and/or aromatic hydrocarbyl, and where both of $X_a$ and $X_e$ are halides;
(ii) selectively activating one of the $X_a$ and $X_e$ halide moieties on the di-substituted pyridine under conditions sufficient to form a mono-metallated, halo-substituted pyridine intermediate;
(iii) reacting the mono-metallated, halo-substituted pyridine intermediate with one or more other reactants under conditions sufficient to form a halo-substituted pyridinyl aldehyde intermediate;
(iv) arylating the halo-substituted pyridinyl aldehyde intermediate by contacting it with an optionally substituted aryl-dihydroxyborane under conditions sufficient to form an (optionally substituted aryl)-substituted pyridinyl aldehyde intermediate;
(v) aminating the (optionally substituted aryl)-substituted pyridinyl aldehyde intermediate by contacting it with one or more other reactants under conditions sufficient to form the crude functionalized pyridyl-amine product;
- (vi) treating the crude functionalized pyridyl-amine product with an acid to form a functionalized pyridyl-ammonium product salt;
- (vii) triturating the functionalized pyridyl-ammonium product salt to remove impurities; and
- (viii) treating the isolated, functionalized pyridyl-ammonium product salt with a base to form a purified functionalized pyridyl amine product;

(b) forming a metal-ligand precursor by contacting the pyridyl-amine product with a metal precursor compound, and optionally also with an activator;

(c) contacting an olefin feed with said metal-ligand precursor under reaction conditions sufficient to produce an effluent comprising a trimerized and/or tetramerized olefin product; and (d) optionally isolating and/or purifying the trimerized and/or tetramerized olefin product.

* * * * *